United States Patent [19]

Klimm et al.

[11] Patent Number: 5,626,129
[45] Date of Patent: May 6, 1997

[54] DEVICE FOR MONITORING AT LEAST ONE CONNECTION IN A MEDICAL TUBING SYSTEM

[75] Inventors: Josef Klimm, Karthauserstrasse, Regensburg, Germany, D-93051; Thomas Schmid, Mintraching, Germany

[73] Assignee: Josef Klimm, Germany

[21] Appl. No.: 346,765

[22] Filed: Nov. 30, 1994

Related U.S. Application Data

[63] Continuation-in-part of PCT/DE94/00356 Mar. 30, 1994.

Related U.S. Application Data

[63] Continuation-in-part of PCT/DE94/00356 Mar. 30, 1994.

[30] Foreign Application Priority Data

Apr. 2, 1993 [DE] Germany .................... 43 10 855.5

[51] Int. Cl.[6] .............. A62B 9/04; A62B 27/00
[52] U.S. Cl. ................ 128/202.22; 128/202.27; 128/205.23; 340/686; 340/687
[58] Field of Search ............ 128/202.22, 202.27, 128/912, 205.27, 207.14, 207.18, 205.23, 204.18, 200.24; 340/573, 686, 687, 605; 285/351, 285

[56] References Cited

U.S. PATENT DOCUMENTS

| | | | |
|---|---|---|---|
| 3,595,228 | 7/1971 | Simon | 128/145.5 |
| 3,942,526 | 3/1976 | Wilder et al. | 128/214 E |
| 4,155,357 | 5/1979 | Dahl . | |
| 4,191,952 | 3/1980 | Schreiber et al. | 128/202.22 |

FOREIGN PATENT DOCUMENTS

| | | |
|---|---|---|
| 314306 | 7/1989 | European Pat. Off. . |
| 2298147 | 3/1976 | France . |

*Primary Examiner*—V. Millin
*Assistant Examiner*—William J. Deane, Jr.
*Attorney, Agent, or Firm*—Graham & James LLP

[57] ABSTRACT

In an arrangement for monitoring a connection between two elements (2, 3) of a medical tubing system, preferably an artificial respiration system, a first sensor element (6) is arranged on the first of both elements (3) and a second sensor element (5) is arranged on the second of both elements (2) in the area of the connection (1). At least one sensor element (6) has at least one signal generator which generates a warning signal when both sensor elements move away from each other beyond a predetermined distance.

15 Claims, 2 Drawing Sheets

5,626,129

DEVICE FOR MONITORING AT LEAST ONE CONNECTION IN A MEDICAL TUBING SYSTEM

This is a continuation-in-part of our copending International Application PCT/DE94/00356, filed Mar. 30, 1994, designating the United States, pursuant to 35 USC §365(c) and 35 USC §120.

FIELD OF THE INVENTION

The present invention relates to a system for monitoring a connection between two tube elements of a medical tube conduction system.

BACKGROUND OF THE INVENTION

Tube conduction systems containing several tube elements which are connected to each other by simple insertion are very frequently employed in medicine. A typical example of this is the connection between a Y-coupler and a tube of a medicinal oxygen-supply system such as used, for instance, in operations together with an anesthesia machine.

The connections can be made rapidly as a result of the insertion. The tube elements of such a connection can, however, become loose. For instance, in the case of the connection between the tube and the Y-coupler of an oxygen-supply system this can lead to serious accidents resulting in death, particularly in the case of a patient who is being completely supplied with oxygen and, in particular, also when active respiration is not possible, due, for instance, to the administration of muscle relaxants.

In addition to this, the tube elements used in medical tube connections are frequently low cost articles which are used only once and therefore are manufactured with relatively large tolerances with respect of their cross-sectional dimensions, so that the danger of disconnection cannot be excluded because of these tolerances.

A system for monitoring the connection between a coupler and a tube of a medicinal oxygen-supply system is known (U.S. Pat. No. 3,595,228). The known system consists essentially of a circuit having an oscillator. By means of an electric connecting line, which extends over ohmic contacts between the tube and the coupler, the oscillator is grounded on the body of the patient, whereby swinging of the oscillator is prevented. If the connection between the tube and the coupler comes loose and the connecting line is thereby interrupted, the oscillator is activated to generate an audio frequency to a loudspeaker of the system.

This known system has the disadvantage that it requires a connecting line on the body of the patient. This is undesirable for reasons of safety. Furthermore, there is the danger that, in the known system, the generation of an audio signal will be suppressed even if, after a loosening of the connection between the coupler and the tube, the coupler should accidently happen to come against the patient so that the oscillator is still grounded on the patient via the probe line, even though the connection to be monitored has been actually interrupted.

An alarm device is also known by which the presence of an infusion liquid in an infusion system is monitored (U.S. Pat. No. 3,942,526). In the known device, a float is provided in a space traversed by the infusion liquid which float moves downward in said space in the absence of infusion liquid and, by means of a permanent magnet, actuates a sensor which is formed by a reed contact. A monitoring system for medicinal tube connections is not conceived in this case.

SUMMARY OF THE INVENTION

The object of the present invention is a system or a device enabling the connection between two tube elements of a medicinal tube system to be monitored in an easy yet nevertheless extremely reliable manner.

In order to achieve this object, a system for monitoring a connection between two tube elements of a medical tube conduction system said system comprises:

A first sensor element provided in the region of the connection on a first one of said two tube elements, a second sensor element provided in the region of the connection on a second of the two tube elements, the first sensor element having at least one permanent magnet generating a magnetic field, the second sensor element being a magnetic field responsive signal transducer formed by a magnetically actuable electrical contact or by an electronic sensor responsive to a magnetic field, with the second sensor element being positioned neighboured to the first sensor element and being actuated by the magnetic field of the permanent magnet of the first sensor element when the two tube elements of the medicinal tube conduction system are connected to one another, and with the second sensor element being deactivated, when the connection of two tube elements has become loose and thereby the two sensor elements are separated from each other by more than a maximum predetermined amount, a monitoring and indicating device connected to the second sensor element for generating an acoustic and/or optical alarm signal when said second sensor element is deactivated.

With the system of the invention, a reliable monitoring of connections of a medicinal tube-line system is possible. In a preferred embodiment of the invention, the active second sensor element is formed by a reed contact and the passive first sensor element is formed by at least one permanent magnet which cooperates with said contact. This embodiment has the advantage of highly reliable operation, while being of simple and strong construction. At least the first element can be provided, in accordance with the invention, firmly on the tube element in question, of the connection or can be made in one piece with said tube element. The permanent magnet can be formed in the manner that a magnetized ferrite material is bound as filler in the material, particularly plastic material, forming the first sensor element.

The problem indicated above with regard to connections in medicinal tube conduction systems can, in particular, also be avoided with the system in accordance with the invention.

The invention will be described in further detail below with reference to an embodiment shown in the drawing, in which:

DETAILED DESCRIPTION OF THE DRAWINGS AND THE PREFERRED EMBODIMENTS

Figure 3:
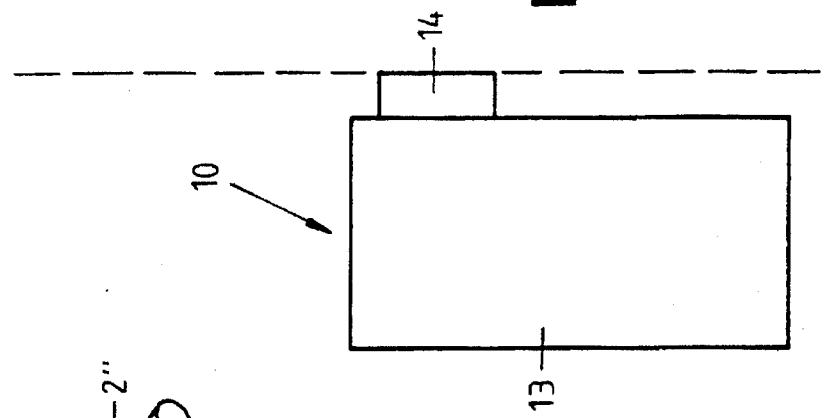
FIG. 3 is a simplified showing, in side view of the housing for the monitoring and indicating electronics.
Figure 1:
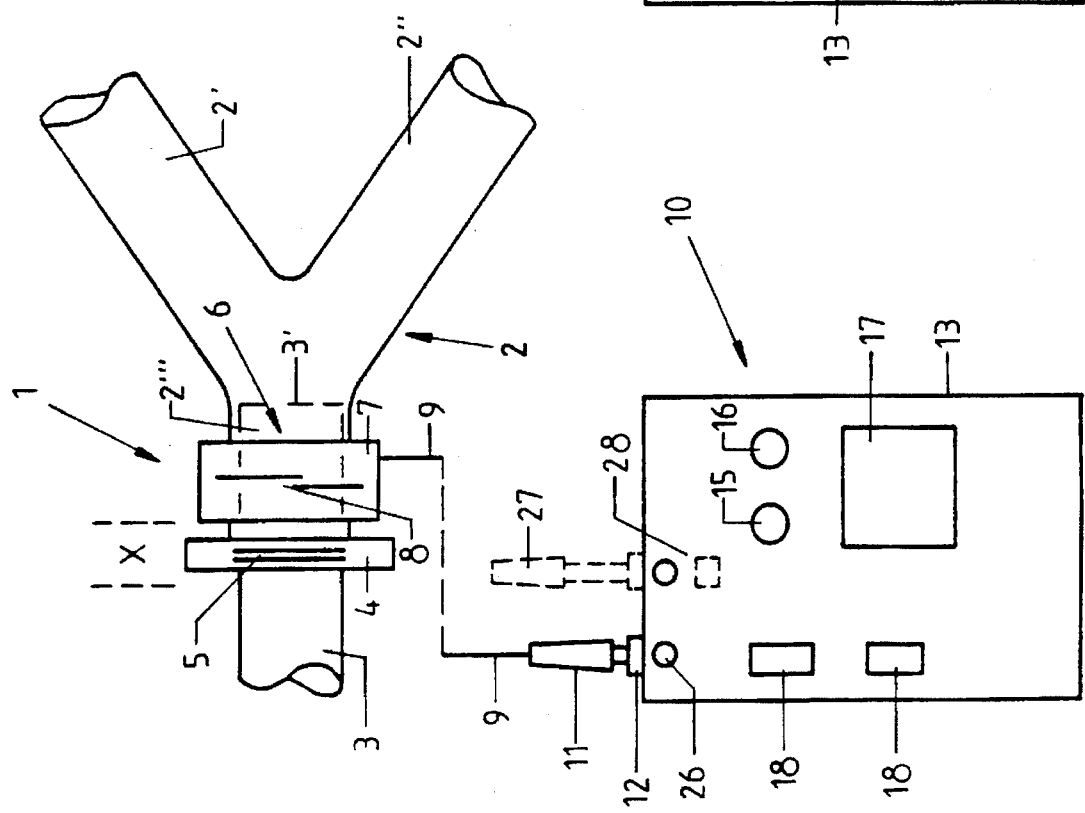
FIG. 1 shows enlarged, a detail view of a Y-coupler and a tube of a medicinal oxygen-supply system which is connected to said Y-coupler, together with the sensor elements which are provided on the tube and on the Y-coupler, and a monitoring and indicating device of the monitoring device of the inventive monitoring system.

In the Figures, 1 designates the connection of two components or tube elements of a medicinal tube conduction system, namely of an oxygen-supply system, specifically between a Y-coupler 2 and a tube 3. The Y-coupler, in known manner, forms an inhalation branch 2' and an exhalation branch 2", by which this Y-coupler is connected to an anesthesia machine (not shown) or to other tube elements (not shown) of an oxygen-supply system. The Y-coupler 2 is connected to the tube 3 at the branch 2''', i.e. the one end of the tube 3 is inserted at the branch 2''' into the Y-coupler 2 and held there by a clamp seat. In the embodiment shown, the tube 3 has at this end a flange 4 which is made of plastic in the same way as the tube 3, and is preferably integral with the tube 3. A permanent magnet 5 is embedded in the flange 4. When the tube 3 is properly connected to the Y-coupler 2, the flange 4 is adjacent a sensor element 6 fastened to the Y-coupler 2. The sensor element 6 consists of a housing 7, preferably of plastic, which is detachably fastened to the end of the Y-coupler 2 forming the branch 2''' by means of a clamp attachment, for instance by means of a clip, preferably by means of a clip development on the housing 7. The fastening means for the sensor element 6 and/or the Y-coupler 2 are so developed that attachment of the sensor element 6 to the Y-coupler 2 is possible only in a position which assures proper operation of the monitoring system. Within the housing 7, the sensor element 6 has a reed contact 8. The latter is developed in such a manner that it is open in the condition of rest or non-activated condition.

If the connection 1 has been properly established and if the flange 4 with the permanent magnet 5 is accordingly directly adjacent the sensor element 6, the reed contact 8 will be closed. Via a connecting cable 9, the reed contact 8 is connected to a monitoring and indicating device 10 by means of a multiple plug 11 which is present on the connecting line and can be inserted into the multiple jack 12 on the housing 13 of the monitoring and indicating device 10.

The monitoring and indicating device 10 can be located at a place suitable for the monitoring. For this purpose, the housing 13 has on its rear attachment magnets 19 for holding the monitoring and indicating device 10 on metal parts. The monitoring and indicating device 10 is so developed that, after the connecting or activating, it monitors the reed contact 8 in a ready state or mode. By means of a first light-emitting diode 15, this connected condition or state of readiness is indicated. A second light-emitting diode 16 provides a blinking light signal in case of an alarm. Furthermore, the monitoring and indicating device 10 has an acoustic signal transmitter 17 which is formed, for instance, of a crystal signal transmitter and, in case of an alarm, gives off an acoustic signal in the form of a pulse-like series of tones.

In detail, the control and monitoring device 10 is so developed that when, upon activation or in ready state, a loosening or even a separation of the connection 1 takes place and the flange 4, together with the permanent magnet 5, has thereby moved over by a predetermined path x away from the sensor element 6, the reed contact 8 opens and in this way a control signal is produced which brings about the optical signal on the light-emitting diode 16 and the acoustic signal transmitter 17. The control and monitoring device 10 is preferably so designed that, once an optical and acoustic alarm has been given, it can only be terminated by depressing a function key 18 provided for this purpose, and only if the connection 1 has been properly reestablished. Of course, the movement distance x which produces the alarm is substantially less than the length 3' by which the end in question of the tube 3 is introduced into the end of the Y-coupler 2 forming the branch 2'''. In this way, assurance is obtained that the alarm will be given in all cases prior to a separating of the connection 1.

Figure 2:
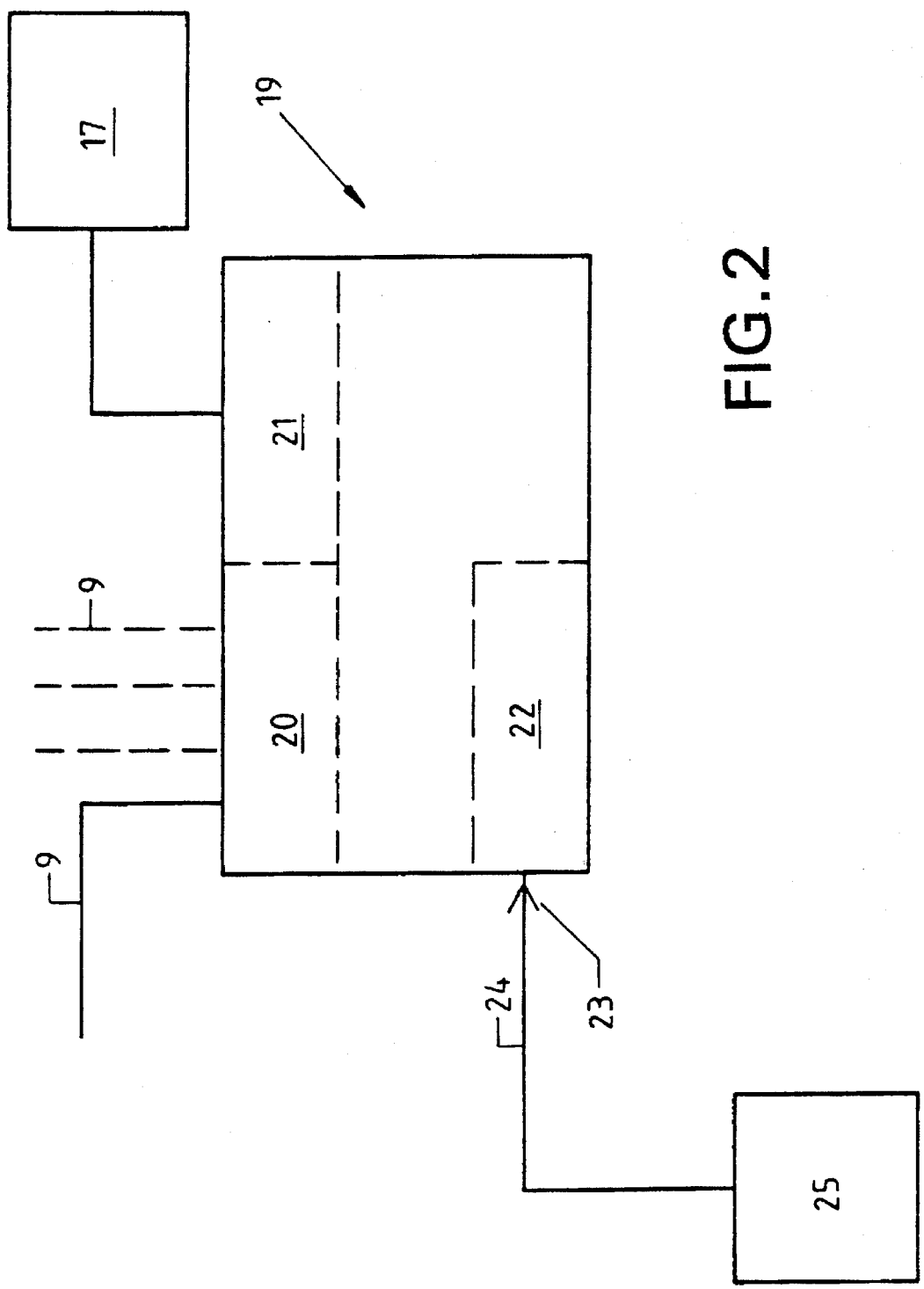
FIG. 2 is a block diagram of the monitoring and indicating device.

FIG. 2 shows the monitoring and indicating device 10 in the form of a block diagram, together with the probe device formed by the permanent magnet 5 and the reed contact 8. Electronics system 19 which includes an input circuit 20 and an output state 21 for driving the acoustic signal transmitter, comprises the monitoring and indicating device and is constructed, for instance, with discrete components or with integrated circuits. The electronics system can, however, also be formed by a microprocessor with corresponding elements.

The monitoring and indicating device 10 further comprises a rechargeable battery 22 which is arranged in the housing 13 and can be connected, via a suitable connector 23 on the housing and a charging cable 24, to a power pack 25.

In principle, the current supply comprising the battery 22 for the electronics system 19 can be arranged such that operation of the monitoring and indicating device 10 is possible even with the power pack 25 connected, so that, upon operation, the battery 22 is also charged. Alternatively, if the battery 22 is exhausted, the operation of the monitoring and indicating device 10 is possible by the connection of the charger 25.

However, the current supply for the electronics systems 19 preferably so developed that operation of the monitoring and indicating device 10 is only possible when the charging cable 24 is not connected to said device. In this way, interference and, in particular, also danger due to a defective charger 25 are avoided during the operation of the monitoring system.

As a result of the battery operation, the monitoring and indicating device is very mobile and can be positioned at any suitable place.

Preferably, several connections 1 and/or the sensor devices provided on these connections and formed by, in each case, a permanent magnet 5 and a sensor element 6 are monitored. For this, the input circuit 20 has several inputs each formed of a jack 12, they being each connected via a connecting line 9 to the sensor device on a connection 1. With the monitoring and indicating device 10 activated, these inputs are then simultaneously monitored or continuously periodically checked by the input circuit 20. If one of the connections 1 is defective, and therefore the reed contact 8 associated with this connection is open, the optical and acoustic alarm is given.

In the case of several inputs or upon the monitoring of several connections 1, in order to be able rapidly to note the defective connection, an optical display 26 is provided on the device 10 or the housing 13, for indicating the defective connection 1 and/or the corresponding output (jack 12). This indicating device consists, for instance, of a plurality of light-emitting diodes, with one light-emitting diode being associated with each output.

The monitoring and indicating device 10 or its electronics system 19 is furthermore so developed that, in ready state, there is only a minimum consumption of current, such that the current consists essentially of the quiescent currents flowing over the reed contacts 8 and the slight amount of current for the light-emitting diode which indicates the ready state. Only in the event of an alarm, is there then a greater need for current, in particular for the giving of the acoustic signal.

In the above description, it has been assumed that the sensor element 6 for the connection 1 which is to be monitored in each case is connected via a connecting cable 9 to the monitoring and indicating device 10. In principle, this connection can also be produced without wires, such as by means of electromagnetic waves or preferably with the use of infra-red light. In such case, each sensor element 6 is developed with a mini-transmitter for a corresponding electromagnetic signal or an infra-red signal and with a current supply (battery) of its own. The monitoring and indicating device 10 has a receiver for signals in the form of electromagnetic waves or infra-red light. This receiver is then, for instance, part of the input circuit 20. If several connections 1 are to be monitored simultaneously, the transmitters associated with the individual sensor elements 6 supply different signals which, after demodulation and/or decoding in the receiver, are applied to the individual connections 1. If the signal of a transmitter is not given, there will, in any event, be the optical and acoustic alarm by means of the light-emitting diode 16 and the signal transmitter 17.

With several jacks 12, in order to be able to monitor a number of connections 1, less than the number of said connectors, dummy plugs 27 are preferably provided, which are being inserted, instead of the plug 11, into the unoccupied connectors or jacks 12, thereby simulating a closed reed contact 8. Instead of this dummy plug, a switch 28 can be associated with each input or each jack 12 on the monitoring and indicating device 10 and on the housing 13 respectively, with each switch 28 being switched into the closed position when the associated jack 12 is not occupied and thereby simulating a closed reed contact.

The invention has been described above on basis of one embodiment. It is obvious that changes and modifications are possible without thereby going beyond the basic concept of the invention.

Thus, it is possible instead of the sensor device 16 having the reed contact 8 also to use other sensors by which the presence of a counterpart provided on the tube 3 can be monitored without contact. For this, there are suitable, (in particular, also inductive of capacitive approximation) sensors which operate without contact, although the sensor element 6 with the reed contact 8 represents a particularly robust embodiment which, in particular, does not require any further supply connections, etc., in addition to the connections of the reed contact. In the place of the reed contact 8, there can also be used a sensor which responds to a magnetic field (Hall sensor).

By the removable attachment of the sensor element 6 from the Y-coupler 2, the latter can also be cleaned and sterilized in the necessary manner. Due to the clip attachment of the sensor element 6, rapid, easy production of the sensor arrangement which monitors the connection 1 is possible.

What is claimed is:

1. A system for monitoring a connection (1) between two tube elements (2, 3) of a medical tube conduction system said system comprising:

a first sensor element (4) provided in the region of the connection (1) on a first one of said two tube elements, a second sensor element (6) provided in the region of the connection (1) on a second of the two tube elements, the first sensor element (4) having at least one permanent magnet (5) generating a magnetic field, the second sensor element (8) being a magnetic field response signal transducer formed by one of a magnetically actuable electrical contact and an electronic sensor responsive to a magnetic field, with the second sensor element being positioned adjacent to the first sensor element and being actuated by the magnetic field of the permanent magnet of the first sensor element when the two tube elements of the medicinal tube conduction system are connected to one another, and with the second sensor element being deactivated, when the connection of two tube elements has become loose and wherein the two sensor elements (4, 6) are separated from each other by more than a maximum predetermined amount, a monitoring and indicating device (10) connected to the second sensor element (6) for generating at least one of an acoustic and optical alarm signal when said second sensor element (6) is deactivated.

2. A system according to claim 1, characterized by the fact that the monitoring and indicating device (10) is a device which is adapted to be arranged separate from the sensor elements (4, 6).

3. A system according to claim 1, wherein the monitoring and indicating device (10) has a housing (13) with at least one holder.

4. A system according to claim 3, wherein said at least one holder is formed of at least one attachment magnet (14) for the attachment of the housing (13).

5. A system according to claim 1, wherein the monitoring and indicating device (10) is a battery operated device.

6. A system according to claim 1, wherein the first and the second sensor elements are each firmly attached to the corresponding element (3) of the connection.

7. A system according to claim 6, wherein the first and the second sensor elements are each made in one piece with one of the two tube elements (2, 3) of the connection.

8. A system according to claim 1, wherein at least one sensor element (6) is removably attached to the corresponding tube element of the connection (1).

9. A system according to claim 1, wherein the second sensor element (6) is connected via a connecting cable (9) to an input (12) of the monitoring and indicating device (10).

10. A system according to claim 1, further comprising at least two sensor devices each comprising first and second sensor elements (4, 6) and monitoring one connection (1), said sensor devices being connected to one monitoring and indicating device (10).

11. A system according to claim 1, wherein the monitoring and indicating device (10) is an electronic system (19) which, after triggering even upon the restoration of an disturbed connection (1) and having an alarm disconnect key (18) for manually deactuating the alarm.

12. A system according to claim 1, wherein said two tube elements of the connection (1) are a Y-coupler (2) of an oxygen-supply system and a tube (3) connected with said Y-coupler.

13. A system according to claim 1, wherein said signal transducer is a reed contact (8).

14. A system according to claim 1, wherein said signal transducer is a hall sensor.

15. A system according to claim 1, wherein the second sensor element is connected with a wireless connection to an input (12) of the monitoring and indicating device (10).

* * * * *